United States Patent [19]

Friedel et al.

[11] 4,210,504
[45] Jul. 1, 1980

[54] METHOD FOR MEASURING THE ELECTROPHORETIC MOBILITY OF PARTICLES

[75] Inventors: Klaus Friedel; Ehrhard Dammann; Hans-Joachim Pohl, all of Jena; Wolfgang Schütt; Hans-Ludwig Jensen, both of Rostock, all of German Democratic Rep.

[73] Assignee: Jenoptik Jena G.m.b.H., Jena, German Democratic Rep.

[21] Appl. No.: 940,793

[22] Filed: Feb. 26, 1978

[51] Int. Cl.² .................. G01N 27/26; G01N 27/28; B01K 5/00
[52] U.S. Cl. .................. 204/180 R; 204/299 R
[58] Field of Search .................. 204/180 R, 299 R

[56] References Cited

U.S. PATENT DOCUMENTS

| 3,909,380 | 9/1975 | Day et al. | 204/299 R X |
| 4,011,044 | 3/1977 | Uzgiris | 204/299 R X |
| 4,046,667 | 9/1977 | Goetz | 204/299 R X |

Primary Examiner—Arthur C. Prescott

[57] ABSTRACT

The invention is in concern of a method for measuring the electrophoretic mobility of particles in a liquid test sample in order to improve the precision of the electrophoretic measurement and to reduce in particular the operational expenditures in such a method.

By use of considerably simple means a very precise time measurement of the mobility of particles is obtained free from any subjective influences with respect to the selection of the particles to be evaluated and to the time measurement. Accordingly, signals variable with respect to their frequency and visualized on the screen of a monitor are derived from out of video synchronization pulses, said signals are logically combined to the digitalized adjustable image scanning signals, improved in their signal-to-noise ratio.

The output signals of this combination effect a counting operation dependent on the particle mobility.

1 Claim, 1 Drawing Figure

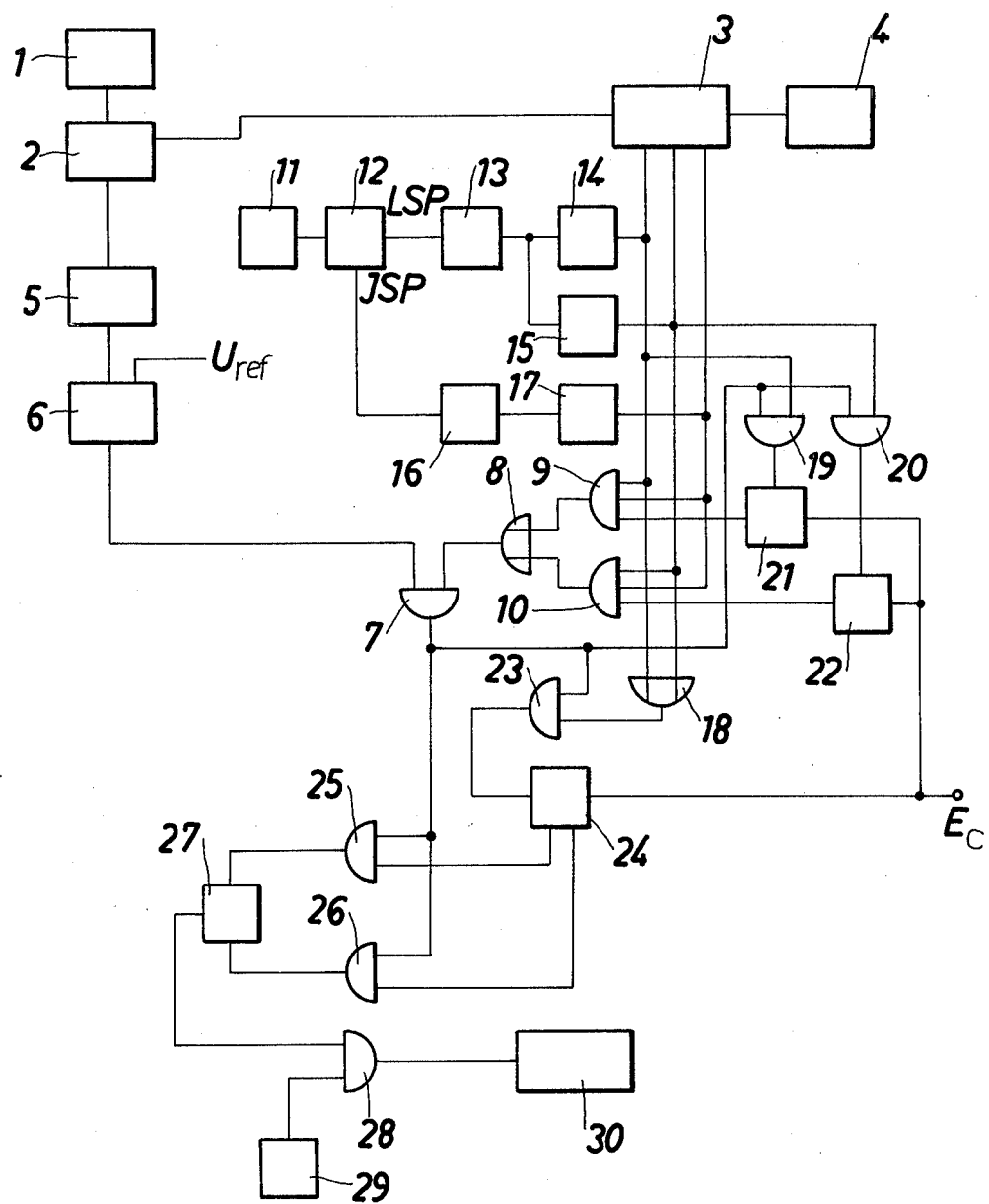

METHOD FOR MEASURING THE ELECTROPHORETIC MOBILITY OF PARTICLES

The invention is in concern of a method for measuring the electrophoretic mobility of particles. A voltage is applied to a liquid sample contained in an electrophoretic cell and the time is measured which a selected particle requires to move a preselected distance between two set markings under microscopic observation of a video image of the sample preferably recorded by means of a vidicon and reproduced on a monitor.

In a previous method and device (Hannig, K.; Wirth, U.; Meyer, B.-M.; Zeiller, K.; "Theoretical and Experimental Investigations of the Influence of Mechanical and Electrokinetic variables on the Efficiency of the Method", Hoppe Seyler's Z. Physiol.Chem., vol. 356) a great number of cells or particles which are fed as a continuous jet into a laminated buffer stream are captured after deflection in a perpendicular electric field in a finite number of chambers, evaluated as to their quantity, and are prepared for further investigations.

The electrophoretic mobility of the particles is determined by the deflection which the particles under investigation undergo in a constant laminar flow.

This method and device is disadvantageous for a number of reasons: The buffer stream and the sample stream require a high constancy, the sample throughput capacity is too low, and repeated investigations are scarcely feasible due to the low-ionic buffer used.

In a further known method the electrophoretic mobility of individual particles is determined out of the Doppler shift of the frequency of the laser light diffused at the particles (Uzgiris, E. E. 1972, Optics Commun 6). The expeditures, multi-channel analyzers etc. have to be employed, with that method for analyzing the diffused laser light are considerable.

Furthermore, a method is known (Vransky, V. K.; "Die Zellelektrophorese", Fortschritte der experimentellen und theoretischen Biophysik, vol. 18), in which the electrophoretic mobility of individual micro-particles is determined by time measurements.

A voltage is applied to a liquid sample in an electrophoretic chamber. Under microscopic observation of the sample the transit time is manually measured (for example, with a stop watch), which a selected and observed particle requires to migrate a preselected distance.

The subjective error which is involved in the measuring result due to the operator is disadvantageous.

The subjective effect depends on the one hand on the visual observation and the manual time measurement and on the other hand, on the operator's decision to select the particles for the time measurement.

To reduce the portion of this subjective measuring error, series of measurements are necessary to obtain the average value which, however, increases the time required for measurements.

At the same time the high operational expenditures are disadvantageous.

It is an object of the present invention to obviate the above disadvantages.

It is a further object of the present invention to provide a method for measuring the precision of electrophoretic measurements and for reducing the technical expenditures, the costs and the time involved in such a method.

It is still a further object of the invention to provide a method for an exact time measurement of the electrophoretic mobility of individual selected particles with the simplest means possible which methods eliminate any subjective error.

The invention is concerned with a method for measuring the electrophoretic mobility of particles including applying a voltage to a sample arranged in an electrophoretic cell, observation of the sample through a microscope, recording by video-technics, displaying upon a monitor, and measuring the time which a selected particle of the sample requires to migrate a predetermined distance, characterised in that an image scanning signal is produced out of the video-record of the sample, the image scanning signal after passing a filter line and subsequent digital conversion by comparison to an adjustable reference voltage is logically connected to pulses which simultaneously arrive at the monitor, one of which is produced by delay out of the image synchronization pulse of the image scanning signal and the other two pulses are provided out of the line synchronization pulses of the image scanning signal, and in that the first signal produced by the logic connection, which signal is produced when one of the delayed line synchronization pulses, the delayed image synchronization pulse and a signal of the digital image scanning signal are simultaneously delivered, triggers a counting operation, which is stopped through a further signal produced by logic combination.

It is advantageous when after the start of the counting operation triggered through a delayed line synchronization pulse, each delayed line synchronization pulse of that delay is rejected and so are any further delayed line synchronization pulses after stopping of the counting operation.

Furthermore, it is advantageous to set the two delay times of the respective delayed line synchronization pulse commonly as well as individually. In addition thereto, it is advantageous when the delay time and the pulse frequency of the delayed image synchronization pulses are adjustable.

It is further advantageous to bright-dark control the monitor through the signals produced from the image and line synchronization pulse and when the signals appear as vertical and horizontal marking lines on the screen of the monitor.

It is still a further advantage when the counting pulses are digitalised and evaluated.

Periodical signals are derived by time delay from the video synchronization pulses, which signals are converted to appear as a rectangle of variable sides upon the screen of the monitor so forming an image section, which is the basis for the time measurement, that is, the time is measured which a particle requires to migrate from one vertical limitation of the image section to the other whenever an electrophoretic particle of the sample to be analysed migrates within said image section.

The time measurement is performed by start and stop of a counting operation, the counting pulses of which can be digitalised and computerised.

The start and the stop of the counting operation is effected through the logic connections, and the delayed video synchronization pulses are effected through the digitalised image evaluation signal of the video-record of the sample. Those delayed line synchronization pulses which have triggered the counting operation are rejected from after the start of the counting operation in order to ensure that the start and the stop of the counting operation are caused at different vertical limitations of the image section on the monitor.

Those particles of the sample which are desired to contribute to the electrophoretic evaluation are selected by balancing the reference voltage relative to the digitalised image scanning signal.

In order that the invention may be more readily understood reference is made to the accompanying drawing which illustrates diagrammatically and by way of example one embodiment thereof and where the FIGURE is a schematical view of an arrangement for performing the inventional method.

A vidicon 1 is connected to a monitor 4 via a separating amplifier 2 and a modulator 3. Simultaneously, the vidicon 1 is connected via the separating amplifier 2, a filter ladder 5 and via a comparator 6 being provided with a reference voltage $U_{ref}$ to the first input of an AND-member 7, the second input of which is connected to the output of an OR-member 8. One input of the OR-member 8 is connected to the output of an AND-member 9, and the other input of the OR-member 8 to the output of an AND-member 10.

A further output of the separating amplifier 2 is connected via an amplitude separator 11 to a pulse distributor 12, a first output of which is coupled to a multivibrator 13 the output of the latter is connected to two further multivibrators 14, 15. The second output of the pulse distributor 12 is connected to respective inputs of the AND-members 9, 10 via two multivibrators 16, 17 connected in series.

The output of the multivibrator 14 is connected to a second input of the AND-member 9, to an input of the modulator 3, to a first input of an OR-member 18, and to a first input of an AND-member 19. In the same manner a connection of the output of the multivibrator 15 is provided to a second input of the AND-member 10 to a further input of the modulator 3, to a second input of the OR-member 18 and to a first input of an AND-member 20. The output of the multivibrator 17 is also connected to the modulator 3 and the output of the AND-member 7 to respective inputs of the AND-members 19, 20.

The AND-member 19 is connected with its output to the reset input of a flip-flop 21, whereas the AND-member 20 is connected to the reset input of a flip-flop 22. The output of the flip-flop 21 is in connection with a third input of an AND-member 9; whereas the output of the flip-flop 22 is connected to a third input of the AND-member 10.

The OR-member 18 and the AND-member 7 are connected with their output side to a respective input of an AND-member 23, the output of which is connected to a reset input of a flip-flop 24.

The set inputs of the flip-flops 21, 22 and 24 are applied to clock pulse input $E_c$. The output of the AND-member 7 is connected to respective inputs of two AND-members 25, 26. A second input of the AND-member 25 is coupled to a first output and a second input of an AND-member 26 to a second output of a flip-flop 24. The outputs of the AND-members 25, 26 are led to two inputs of a flip-flop 27, the output of which is connected to an input of an AND-member 28.

The output of the AND-member 28, to the second input of which a clock pulse generator 29 signal is applied, is connected to a counter 30. The vidicon 1 produces a image signal of a liquid sample to be analysed in which particles are contained (not shown in the drawing for reason of more simplicity).

The video signal is converted into a respective image displayed on the screen of a monitor 4. The vidicon 1 further produces an image evaluation signal, the signal-to-noise ratio of which is improved in the filter ladder 5. This image evaluation signal is digitalised in the comparator 6 in comparing the former to the reference voltage $U_{ref}$ so that the digitalised image evaluation signals arrive at the AND-member 7.

In the amplitude separator 11 the synchronization pulses are derived from the video signal separated in the separating stage 2 and are divided into image synchronization pulses (ISP) and line synchronization pulses (LSP) in the subsequent pulse distributer 12.

The LSP is delayed in the multivibrator 13.

The two multivibrators 14, 15 having different delay times are in series with the multivibrator 13 so that the outputs of the multivibrators 14, 15 provide two delayed periodical line synchronization pulses in time sequence which scan the monitor 4 bright-dark via the modulator 3 and which are rendered visible as two vertical markings on the screen of the monitor.

The position of these markings are either commonly varied by variation of the delay time of the multivibrator 13 or individually by variation of the delay time of the multivibrators 14, 15. These markings limit the distance which is the base of the time measurement of the particles in the sample to be analysed.

The image synchronization pulse (ISP) at the output of the pulse distributor 12 is two times delayed through the multivibrators 16, 17 so that a delayed periodical image synchronization pulse is provided at the output of the multivibrator 17. The leading edge of the pulse is determined with respect to time through the multivibrator 16 and the trailing edge of the pulse is determined through the multivibrator 17. The delayed ISP also produces a horizontal marking on the screen of the monitor 4 via the modulator 3 and the dark-bright control of the monitor 4, the width of the marking depends on the set delay time of the multivibrator 17.

By variation of the delay time through the multivibrator 16 the space between the upper limitation line of the horizontal marking and the upper image margin of the monitor 4 can be adjusted.

Thus, the three markings on the screen of the monitor 4 represent a rectangular image section adjustable at will, which is utilized, according to the invention, for measuring the time of a sample particle, that is, the transit time is measured which a selected particles requires to pass said image section between the two vertical markings.

The time measurement, however, only takes place when the particle also moves within the horizontally limited image section. The selection based, for example, on the size and/or the brightness, which particles have to be electrophoretically evaluated, is carried out by balancing the reference voltage $U_{ref}$ when the ISPs are digitalised in the comparator 6.

The arrangement as shown in the drawing is set into a stand-by position for measuring through a pulse at the control input $I_c$ by setting the flip-flops 21, 22, 24, which considered from the operation technical viewpoint can be executed after preparation of the sample to be analyzed.

In this stand-by position of the arrangement a pulse is produced at the output of the AND-member 7 by the connection of the AND-members 7, 9, 10 and the OR-member 8 when, and only when the delayed ISP, one of the two delayed line synchronization pulses, and a pulse of the digitalised ISP occur at the same time. In this event, the flip-flop 27 is set through the output signal of the AND-member 7 via the AND-member 25, opened through the set flip-flop 24, which flip-flop 27 opens the gate circuit, consisting of the AND-member 28 so that the counting frequency of the clock pulse generator 29 is fed into the counter 30.

The next pulse, produced under the above conditions which arrives at the output of the AND-member 7 resets the flip-flop 24 via the OR-member 18 as well as via the AND-member 23, which flip-flop 24 resets the flip-flop 27 via the AND-member 26.

Through this resetting of the flip-flop 27 the AND-member 28 is blocked and the counting operation of the counter 30 is stopped.

The result of count is digitalised and computer evaluated in relation to the desired time measurement.

Through a new pulse at the control input $I_c$ the arrangement is put into a stand-by position for the next measurement. The counting operation in the counter 30 is started when a selected particle in the sample to be analysed passes one of the two vertical markings.

To prevent a break of the counting operation of the counter 30 when another particle of the same kind in the sample passes that vertical marking which causes the start of the counting operation of the counter 30 each further delayed LSP of the respective delay time is rejected after the start of the counting operation.

This is achieved by connecting the output of the AND-member 7 to the outputs of the multivibrators 14, 15 in the AND-members 19, 20 and the subsequent flip-flops 21, 22 which are coupled to the AND-members 9, 10. The pulse which is delivered at the output of the AND-member 7 and which is responsible for the start of the counting operation resets either the flip-flop 21 via the AND-member 19, or the flip-flop 22 via the AND-member 20.

Which of the two flip-flops 21, 22 is reset depends on whether a delayed LSP triggers the counting operation at the output of the multivibrator 14 or of the multivibrator 15, that is, which vertical marking on the screen of the monitor 4 is passed by a particle of the sample.

The AND-member 9 or the AND-member 10 is blocked, depending on whether the flip-flop 21 or 22 is reset, that is, that one of the periodically delayed LSP of the multivibrator 14 or 15, which triggers the counting operation and which effects a setting of the flip-flop 21 or 22 and 27, cannot produce a stop-pulse for the counting operation of the counter 30 at the output of the AND-member 7.

Hence, the stop of the counter 30 operation is only effected by the other delayed LSP at the input of one of the two AND-members 9, 10 not blocked by one of the two flip-flops 21, 22 at the simultaneous presence of a delayed image synchronization pulse and a pulse of the digitalised image scanning signal.

The multivibrators 14, 15 are followed by pulse shaper units (not shown in the drawing) for pulse shaping of the delayed line synchronization pulses.

The inventional measuring method is not only restricted to time measurements when used for measuring electrophoretic movements of particles in a liquid sample.

We claim:

1. Method for measuring the electrophoretic mobility of particles comprising the steps of applying a voltage to a sample contained in an electrophoreses chamber including the particles to be measured, microscopically observing said sample, producing an image signal by a vidicon from said sample, said image signal including image synchronization pulses and line synchronization pulses, converting said image signal into an image of said sample on the screen of a monitor feeding the image signals into a filter line, subsequent thereto comparing said image signal to an adjustable reference voltage and converting thereby said image signal into a digitalised image signal, producing a first pulse obtained from the image synchronization pulse by adjustable delay and imaging said first pulse on the screen of said monitor, producing a second and a third pulse from out of the line synchronization pulse by adjustable delay and imaging said second and third pulse on the screen of the monitor, logically combining said first, second and third pulse and said digitalised image signal, and obtaining from the logical combination a first and a second signal, said first signal starting a counting operation, said second signal stopping said counting operation.

* * * * *